US007970632B2

(12) United States Patent
Ambrose

(10) Patent No.: US 7,970,632 B2
(45) Date of Patent: Jun. 28, 2011

(54) HEALTH INSURANCE SUBROGATION DATA MANAGEMENT

(76) Inventor: Stephen Ambrose, Richmond, VA (US)

( * ) Notice: Subject to any disclaimer, the term of this patent is extended or adjusted under 35 U.S.C. 154(b) by 348 days.

(21) Appl. No.: 12/267,087

(22) Filed: Nov. 7, 2008

(65) Prior Publication Data
US 2010/0049544 A1  Feb. 25, 2010

Related U.S. Application Data

(60) Provisional application No. 61/091,721, filed on Aug. 25, 2008, provisional application No. 61/099,202, filed on Sep. 23, 2008.

(51) Int. Cl.
G06Q 10/00 (2006.01)
(52) U.S. Cl. ............ 705/3; 705/2; 705/4; 707/603
(58) Field of Classification Search .......... 705/2–4; 707/603
See application file for complete search history.

(56) References Cited

U.S. PATENT DOCUMENTS

| 4,491,725 A * | 1/1985 | Pritchard ............ 705/2 |
| 2001/0051879 A1* | 12/2001 | Johnson et al. ............ 705/2 |
| 2007/0179818 A1* | 8/2007 | Magnus ............ 705/4 |

* cited by examiner

Primary Examiner — Gerald J. O'Connor
Assistant Examiner — Sind Phongsvirajati

(57) ABSTRACT

A computer-implemented method where a party other than the patient's health plan, requests patient records from a health provider, thereby triggering the health provider to submit identifying demographic data of the requesting party and additionally, if different, the name of the health provider's patient for whom the party requested records on, where the submission by the health provider is made to the patient's health plan, allowing the health plan to gain improved knowledge on the patient's involvement in an injury claim, thereby improving the health plan's subrogation operations.

7 Claims, 20 Drawing Sheets

PROVIDER:                                                             PCI #

CERTIFICATION OF RECORDS REQUEST (CORR)

1. For the dates of service/treatment asked for within the records request, do you have information indicating that the patient had: (check all applicable)

\_\_\_\_ PRIVATE HEALTH INSURANCE? (HMO, PPO, POS, Federal, State, Medicare Supplement, etc.)
      \_\_\_\_ MEDICARE or MEDICAID?
      \_\_\_\_ ANY TYPE OF HEALTH BENEFIT, TO HELP PAY FOR THEIR HEALTH SERVICES RECEIVED?

☐ YES         *If YES, then answer the rest of the questions and fax in this form with request pages and payment statement to PCI. If NO, then put an 'X' through rest of questions below.*         ☐ NO 2. PATIENT'S NAME (print) _____ DATE: _____

Patient Social Security #: _____
     Patient Health Insurance: _____
     Insurance Policy # _____ Insurance Group # (if available) _____

3. PARTY REQUESTING RECORDS:   ☐ Attorney/Legal Firm   ☐ Insurance Co.   ☐ Patient/Guardian
     Party Name: _____ Phone (with area code) (\_\_\_\_) _____
     Address (street, city, state, zip): _____

4. PREVIOUSLY FAXED PAC FORM BARCODE NUMBER (if applicable): _____

THE NEXT THREE QUESTIONS _ARE ONLY ANSWERED_ IF THE RECORDS REQUEST HAS BEEN MADE BY THE PATIENT or THEIR LEGAL GUARDIAN.

5. Are Your Requested Records Related to ANY OF THE FOLLOWING? (check all applicable)

\_\_\_\_ An injury involving another person or entity (on-the-job, auto, slip/fall, assault, etc.)
      \_\_\_\_ An injury claim or lawsuit for which you have retained or plan to retain an attorney
      \_\_\_\_ An injury claim that you plan to file to an insurance company responsible for your injury
      \_\_\_\_ A large lawsuit where you are one of many parties suing a single business or industry
      \_\_\_\_ None of the above 6. Will you be using these records as part of a claim filed to your own auto insurance for payment?
     ☐ Yes   ☐ No   ☐ Not Applicable    If yes, name of your auto insurance _____

7. If you have an Attorney and/or an Injury Claim #:    ☐ Not Using An Attorney    ☐ No Claim #
     Attorney / Firm: _____ Phone (with area code) (\_\_\_\_) _____
     Attorney Address: _____
     Injury Claim #: _____ Insurance Co. Name: _____

FIG. 6

PROVIDER: _____     PCI # _____

Patient Attestation to Existence of Injury and/or Lawsuit Claim (PAC)

1. DO YOU HAVE ANY OF THE FOLLOWING? *(check all applicable)*

_____ Private health insurance? *(HMO, PPO, POS, Federal, State, Medicare Supplement, etc.)*
    _____ Medicare *or* Medicaid?
    _____ Any plan not mentioned above, which pays for health services? WHICH? _____

☐ YES    | If YES, then answer question 2 below.<br>If NO, then cross out all questions below with an 'X' |    ☐ NO 2. IS YOUR VISIT TODAY RELATED TO ANY OF THE FOLLOWING? *(check all applicable)*

_____ An injury involving another person or entity (on-the-job, auto, slip/fall, assault, etc.)
    _____ An injury claim or lawsuit for which you have retained *or* plan to retain an attorney
    _____ An injury claim that you plan to file to an insurance company responsible for your injury
    _____ A large lawsuit where you are one of many parties suing a single business or industry ☐ YES    | If YES, then answer questions 3-9 below.<br>If NO, then cross out all questions below with an 'X' |    ☐ NO 3. PATIENT LEGAL NAME *(PRINT CLEARLY)* _____
    SOCIAL SECURITY #: _____  DATE _____

4. HEALTH INS. CO: _____ POLICY # _____ GROUP # _____

5. ACCIDENT / INJURY DATE: mo. _____ / day _____ / year _____  ACCIDENT LOCATION (state): _____

6. Was your accident or injury due to the fault of another person/entity, your fault or an on-the-job injury?
    ☐ Due to another   ☐ My Fault   ☐ On the job – Company Name _____

7. If the injury was due to a vehicular accident, was there a ticket issued? To whom was it given?
    ☐ I got a ticket   ☐ The other person got the ticket   ☐ No ticket was issued   ☐ N/A 8. If injury was from a vehicular accident, do you plan to file a claim to *your own auto insurance* through:
    ☐ Med Pay / PIP   ☐ Uninsured Motorist   ☐ No-Fault   ☐ Not Sure   ☐ N/A
    NAME OF YOUR *AUTO* INSURANCE *(if applicable)*: _____

9. If you have retained an ATTORNEY and/or have an INSURANCE CLAIM #: *(write 'N/A' if not applicable)*
    NAME OF YOUR LEGAL FIRM or LAWYER: _____
    LEGAL FIRM or LAWYER'S ADDRESS, CITY, STATE: _____
    LAWYER'S PHONE NUMBER (with area code): (_____) _____
    INSURANCE CLAIM #: _____ INSURANCE CO. NAME: _____

FIG. 12

HEALTH INSURANCE SUBROGATION DATA MANAGEMENT

CROSS-REFERENCE TO RELATED APPLICATIONS

This application claims the benefit of U.S. Provisional Application No. 61/091,721, filed Aug. 25, 2008, entitled "Subrogation Identification and Collection Method Utilizing Exchanged Information Between Health Providers and Patients," and U.S. Provisional Application No. 61/099,202, filed Sep. 23, 2008, entitled "Method of Subrogation Investigation and Qualification Shared Between a Health Provider and Health Insurer," which are hereby incorporated by reference in their entirety.

BRIEF DESCRIPTION OF THE DRAWINGS

FIG. 6 is an example of a collection data medium, for use with the data collection, reporting and receiving processes of the first embodiment of the computer-based method of data exchange.

FIG. 12 is an example of a questionnaire medium, for use with the data collection, reporting and receiving processes of the second embodiment of the computer-based method of data exchange.

DETAILED DESCRIPTION OF EMBODIMENTS

Figure 1:
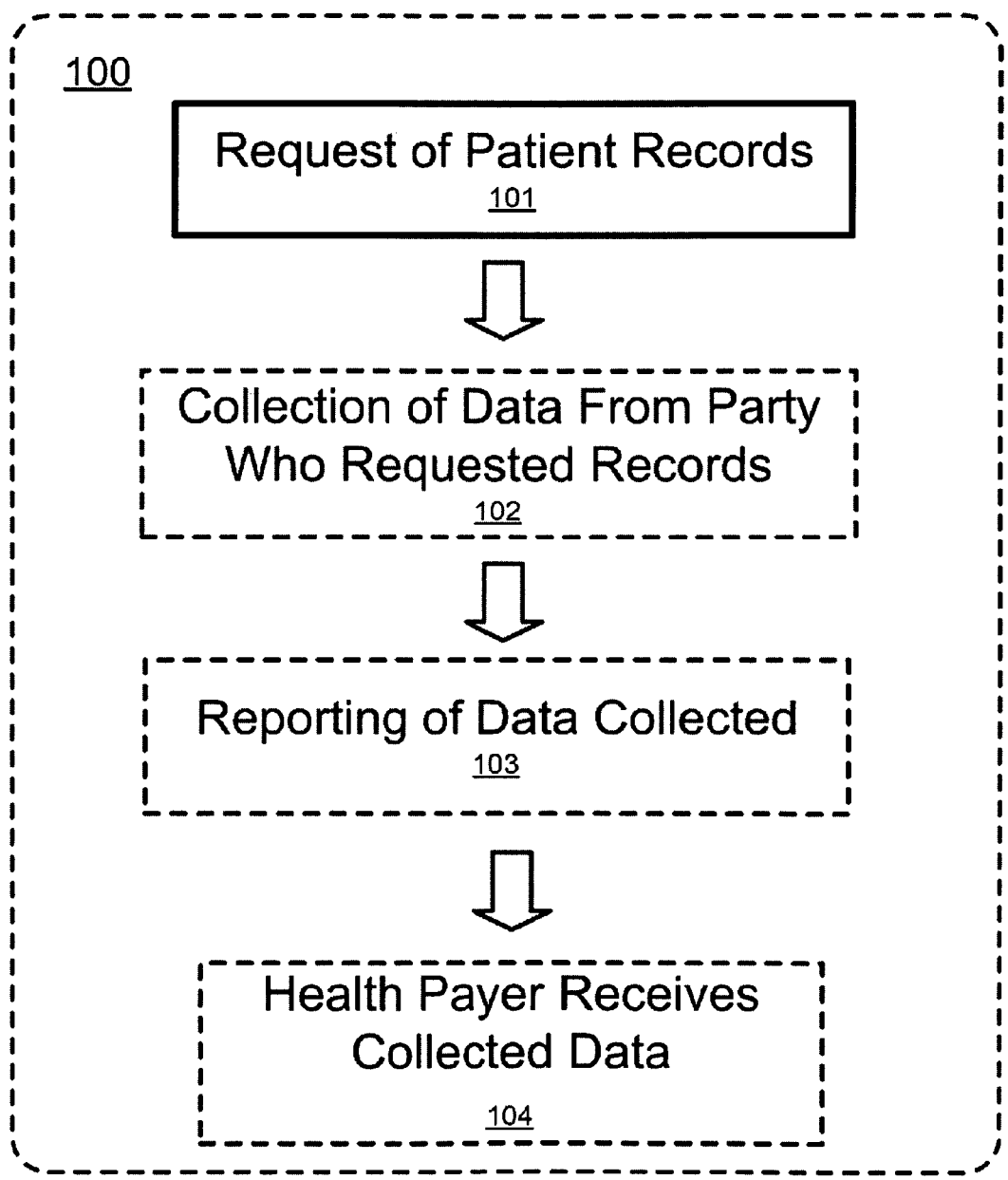
FIG. 1 is an illustration pertaining to the first embodiment of a computer-based method of data exchange between a health provider and a health insurance company, specific to data relating to a request of patient records.

Embodiments of the current invention relate to a computer-based system for exchanging data between a health provider and a patient's health insurance company, where the data involves the health provider's collection of unique information from a patient or their legal representative, when either or both jointly are involved in an injury claim. Subsequently, this collection of information is submitted to the patient's health insurance company for purposes of investigating and identifying opportunities for health insurance company subrogation and recovery.

Subrogation is a legal term, which means that a party, for example, a health insurance company, who has previously paid expenses or debt for a second party, such as a policyholder or claimant, has the ability to assume the legal rights of a person for whom such expenses or debt had been paid.

An example of subrogation would be a health insurer, who has received and subsequently paid upon a health provider's billings, where such billings relate to treatment and care received by the patient, who is also the health insurer's policyholder, specifically as the result of an injury, accident or act of negligence, where the patient's injury was caused by a responsible party other than the patient.

Subsequently, if the patient decides to submit the same health provider billings, which were previously paid by their health insurance company, to a non-health insurance payment party who is responsible for the patient's injuries, and the non-health insurance payment party pays monies relating to those same previously paid billings to the patient or their legal representative, the patient's health insurance company has a legal right to recover the monies they had previously paid out, by filing a subrogation claim against the patient or the settlement relating to their injury claim. Such a claim stipulates that the patient or their attorney pay back the patient's health insurance company.

Subrogation is a legal remedy used in all areas of the insurance industry; however, the method herein is focused specifically on health insurance company-related subrogation. Private and public health insurance companies, as well as Medicare, Medicaid and state or federal government health insurers and programs typically employ health insurance subrogation. Subrogation is a practice supported by both state and federal law. Moreover, many attorneys perform subrogation services for clients as a staple of their practice.

Opportunities for subrogation do not always readily present themselves to the health insurance industry. This is because health insurance companies generally look at the health provider claims sent to them and thereby effect transactions only on general pieces of information, such as the data, sent by the health provider through their insurance claim form.

This data, although not always given by the health provider, aids the health insurance company in finding the potential for subrogation opportunity and subsequent collection. These sections are vague in nature and require a substantial amount of follow-up by the health insurance company and/or their outsourced subrogation department.

Subrogation is highly dependent upon methods of analyzing, auditing and tracing previously submitted health financial records through tedious investigation, and then contacting either the health provider or the patient, in order to determine if the patient came to see the health provider, specifically for an injury, which could have an applicable patient injury claim. Typically, this is not very efficient, due to lack of cooperation from the health provider, poor notation on the claim form, inefficient subrogation methodology and dishonesty or lack of response from the patient on insurance inquiries about injuries.

While more and more health insurance companies are looking to recoup their payouts, when possible, there has never been a strong effort to include the healthcare community to partner and share, with the health insurers for subrogation to any major extent.

Through the system and method presented, there exists an exchange of data between the health provider and the patient's health insurance company, whereby the health provider has a the unique opportunity to both ask for and collect stronger types of subrogation-opportunity information from the patient, thereby having a more quantitative and qualitative effect on the patient's health insurer's ability to investigate, find, monitor and collect upon existing subrogation opportunities.

Such patient-provided information, which the health provider exchanges with the patient's health insurance company, includes two separate events, pertinent to identifying the best opportunity and information for subrogation investigation and identification. These events include when a part requests records for a patient and when the patient checks-in, at a time prior to receiving care.

During the process of requesting patient records, a patient, insurance company or attorney asks for a patient's health information, including treatment notes and/or billings.

Generally, when attorneys request a patient's records from a health provider, there is a strong possibility that such records will be used within an injury or negligence claim. Therefore, the health provider uses this opportunity to note the patient records request and send the information, along with identifying information of the requesting party to the patient's health insurance company.

During the process of the patient's initial registration or check-in, the patient, at a time prior to rendering of care, completes a questionnaire given by the health provider. This questionnaire asks the patient for information, specific to any applicable injury that the patient presents with for needing care, where the injury has an at-fault or liable party, other than the patient.

If such an event is indicated, a number of related follow-up questions asked by the health provider and answered by the patient help in establishing information, which is qualified to be passed from the health provider to the patient's health insurance company.

Because health providers are rendering an important service in setting aside such opportunistic information, this method identifies them as providing exceptional and needed value to the process of subrogation and furthermore, to a health insurer's bottom line collections in regard to subrogation. By using this exchange of information, the health insurance companies have the option to make a payment to the health provider, in consideration for value of such.

According to FIG. 1, a first embodiment of the system and method 100 shows a request made to a health provider's office for a patient's records 101. This occurs at a time concurrent with or after the patient receives care from the health provider.

During the request of patient records 101, the health provider begins the process of collecting data 102. The data collected consists of identifying aspects of both the party making the records request, as well as the patient, whose records have been requested. Subsequently, the health provider determines that through the process of collecting data 102 that such information is qualifies as being reportable to the patient's health insurance company.

The data collected through process 102 is gathered, organized and subsequently goes through a reporting process 103 to the patient's health insurance company.

In the receiving process 104, the patient's health insurance company receives the data, obtained through the collection process 102 and sent to the patient's health insurance company via the reporting process 103.

Figure 2:
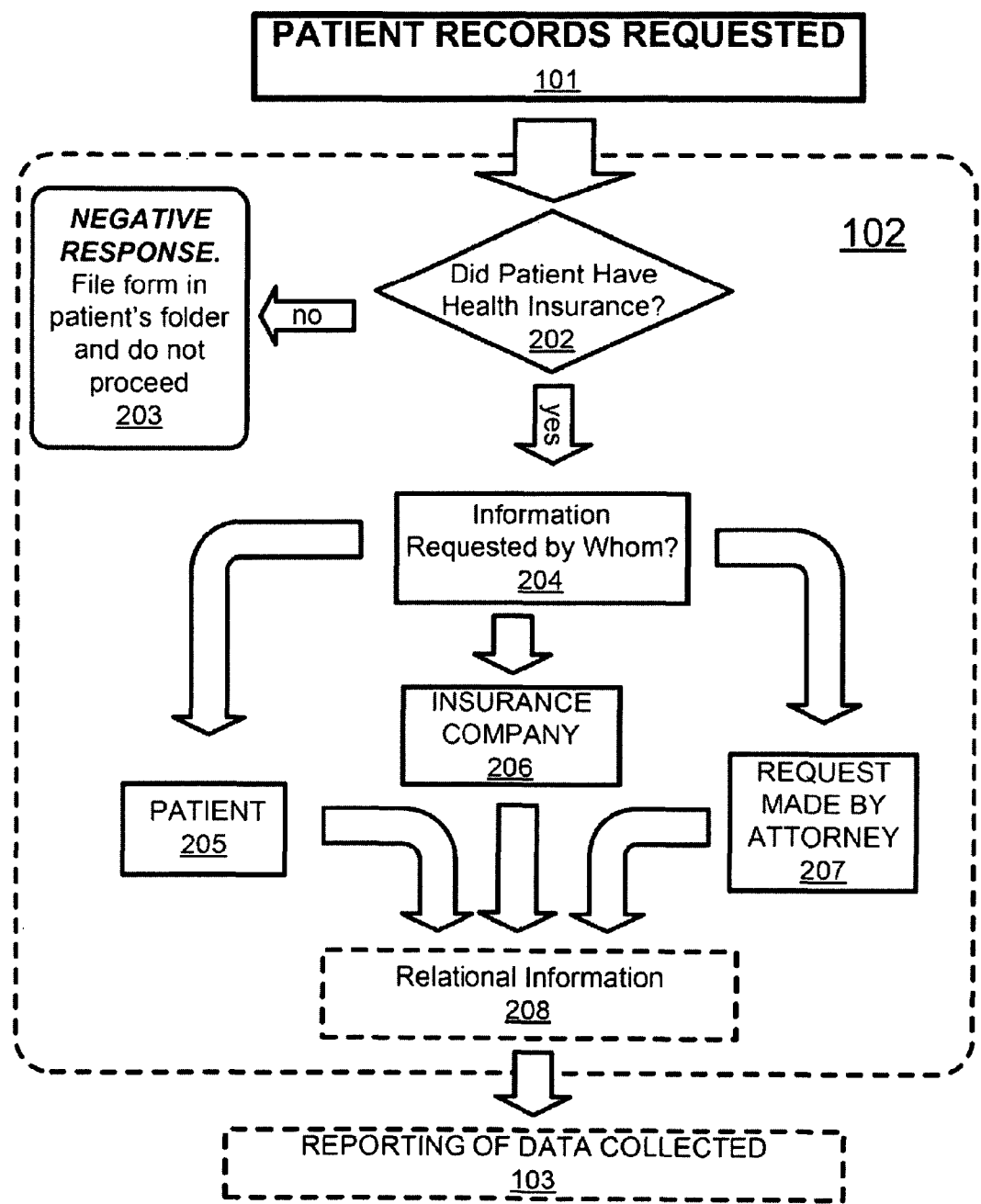
FIG. 2 is an illustration of the data collection process, inherent to the first embodiment of the computer-based method of data exchange.

In FIG. 2, the process of data collection 102 for the first embodiment is further specified in detail.

Data collection process 102 begins with the health provider's use of either a paper-based or electronic medium for collection, allowing for the health provider to gather data related to identifying aspects of both the party making a request of patient records, as well as the patient, whose records are being requested.

The medium used in data collection process 102 has a number of questions, which the health provider and patient jointly complete, when applicable.

The first question of the collection medium 202, asks if the patient had health insurance coverage, during the period they received treatment from the health provider. The health provider checks the patient's records to determine the answer to this question.

If the patient did not have health insurance during their care, then the collection medium is either filed away or discarded 203. Consequently, the process of data collection 102 is halted and the collection medium is deemed non-reportable data.

If the patient did have health insurance coverage during their care, then the health provider continues by determining the type of party requesting the patient records 204. This is important in the health provider determining which type of data to collect in the collection medium.

The party requesting the patient records 204 is either the patient 205, whom the records relate to, an insurance company 206, or an attorney 207 who represents at least one of the following: the patient, as a plaintiff in an injury claim and/or a defendant in an injury claim, where the patient is involved as a plaintiff.

The health provider then gathers the relational information 208 of the party requesting the records. After this is complete, the process of data collection 102 is finished and the collected data goes through the reporting process 103.

Figure 3:
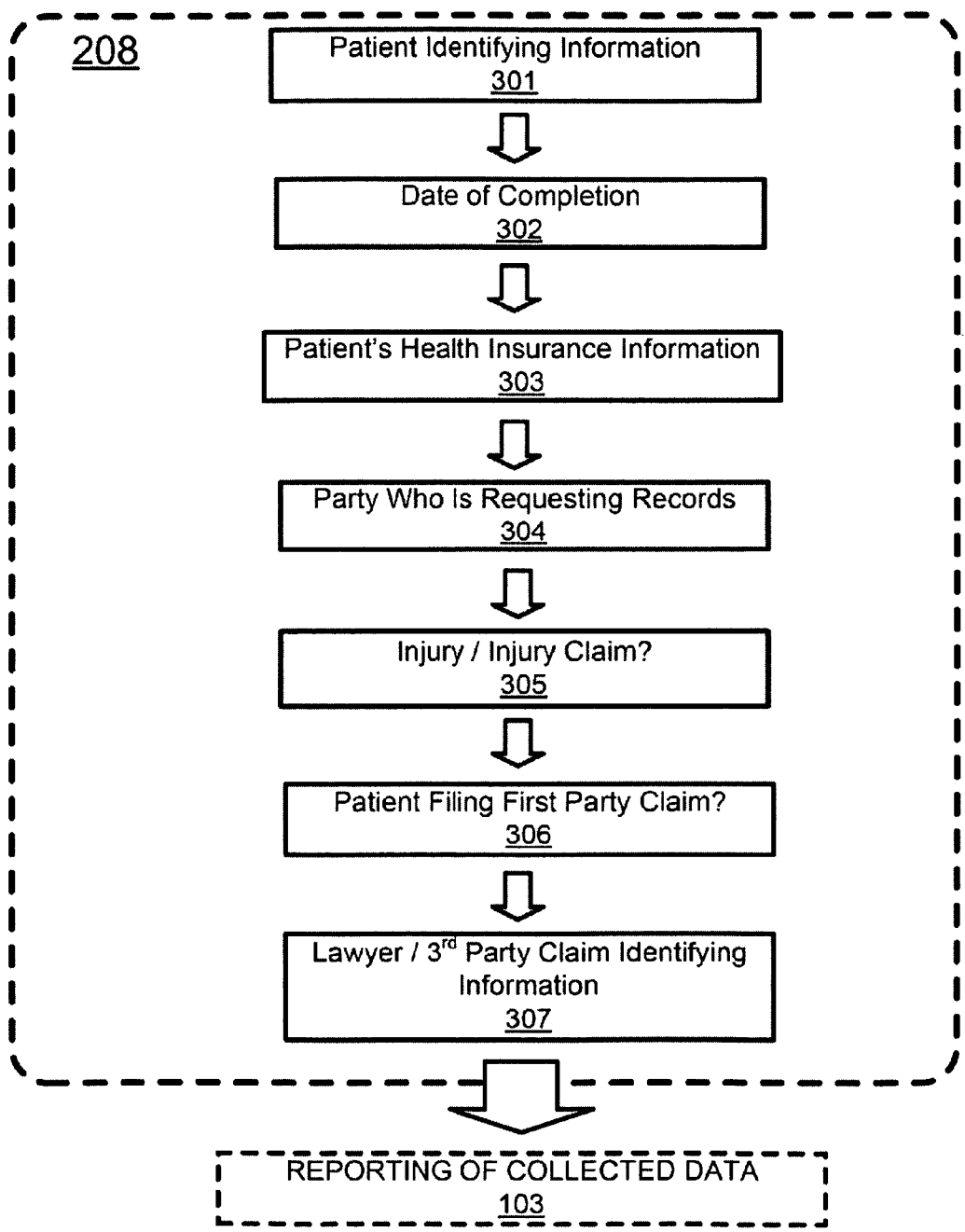
FIG. 3 is an illustration, identifying the relational information portion of the data collection process, inherent to the first embodiment of the computer-based method of data exchange.

FIG. 3 shows the relational information portion of collection medium 208 in greater specificity, inclusive of a number of underlying queries.

The first query 301 of the relational information portion of the collection medium 208 requests the identifying information of the patient 301, including the patient's name, social security number and home state of residence.

The second query 302 of the relational information portion of the collection medium 208 requests the current date on which the collection medium is being filled out.

The third query 303 of the relational information portion of the collection medium 208 requests the patient's health insurance information, which includes the name of the patient's health insurance company, the policy number and the group number of their health plan.

The fourth query 304 of the relational information portion of the collection medium 208 requests classification of the party who is requesting the patient records, be it a patient, insurance company, or attorney. Additionally in query 304, the health provider ascertains the name and identifying information of the party requesting the patient's records.

The fifth query 305 of the relational information portion of the collection medium 208 asks the patient, if they are the requesting party, whether or not they are requesting their records for use with at least one of the following: an injury involving another person or entity, an injury claim or lawsuit for which the patient has retained or plans to retain an attorney, an injury claim that the patient plans to file to an insurance company responsible for their injury and/or a large lawsuit where the patient is one of many parties suing a single business or industry (class-action lawsuit).

The sixth query 306 of the relational information portion of the collection medium 208 asks the patient, as the requesting party, if they have and/or will be filing a first party injury claim. The first party injury claim includes a patient's attestation that the filing of the claim was and/or will be to at least one of the following: Med Pay, Personal Injury Protection (PIP), Uninsured Motorist, Underinsured Motorist and/or No-Fault.

The seventh query 307 of the relational information portion of the collection medium 208 requests the patient's attestation relating to whether or not they have secured an attorney and/or have an active third party claim with a responsible non-health insurance company.

Moreover, if the patient attests positively to query 307 for having an attorney, then they complete the identifying information relating to the attorney, including the attorney's name, phone number and address.

If the patient attests positively to query 307 for having an active injury claim with a third party insurance company, then they complete identifying information relating to the injury claim number and third party insurance company name.

After all the queries as part of the relational information portion of the questionnaire 208 have been completed, the health provider reports the collected data through process 103.

Figure 4A:
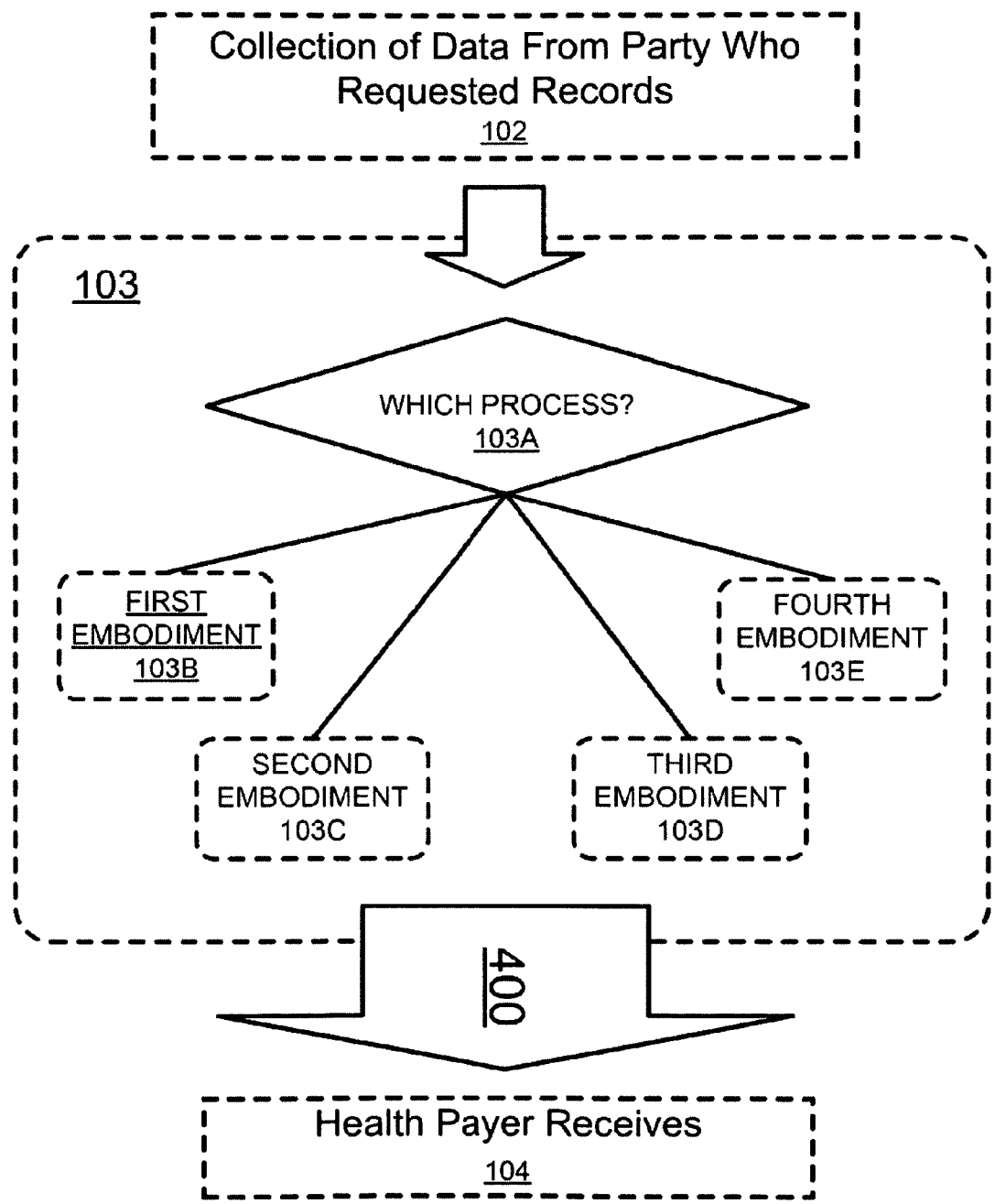
FIG. 4A is an illustration, demonstrating four different embodiments of the reporting process, inherent to the first embodiment of the computer-based method of data exchange.

FIG. 4A demonstrates the collected data 102 sent to the patient's health insurance company 104 through a reporting process 103. Moreover, in 103A, the health provider chooses one of the different embodiments of the reporting process 103, where the embodiments of the reporting process include 103B, 103C, 103D and 103E.

The health provider makes a choice of embodiment process and subsequently reports via 400, the collected data in 102 to the health insurance company, who takes possession of the data through a receiving process 104.

Figure 4B:
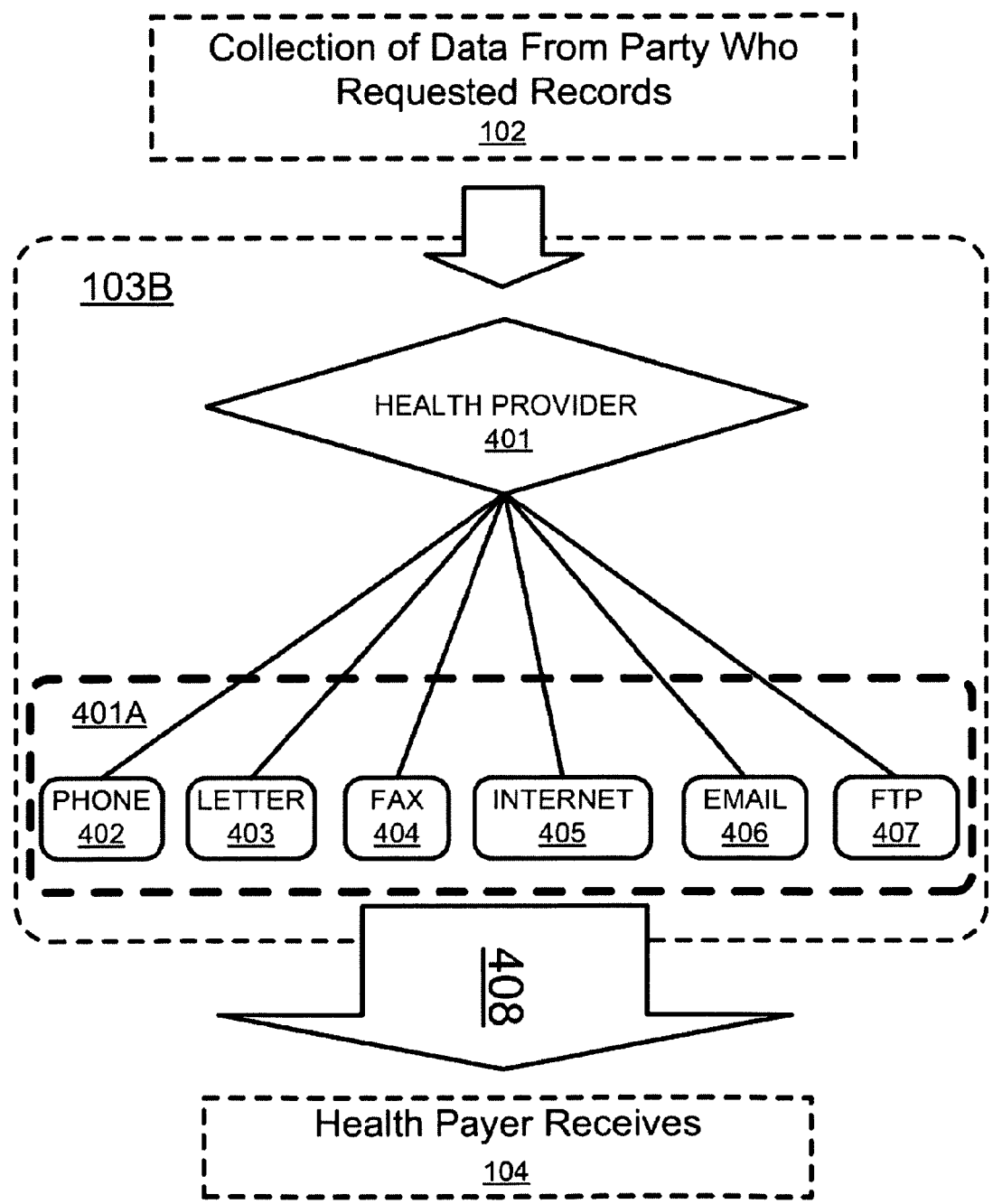
FIG. 4B is an illustration, specifying the first embodiment of the reporting process, inherent to the first embodiment of the computer-based method of data exchange.

FIG. 4B shows the first embodiment of the reporting process 103B, which takes collected data 102 gathered by the health provider 401 and transfers the data to the health insurance company 104 through a choice from a grouping of data transfer methods 401A, including at least one of the following: phone 402, letter 403, fax 404, internet 405, email 406 and/or file transfer protocol (FTP) 407.

The health provider 401 makes a choice of data transfer method from grouping of data transfer methods 401A, and subsequently reports via 408, the collected data in 102 to the health insurance company, who takes possession of the data through a receiving process 104.

Figure 4C:
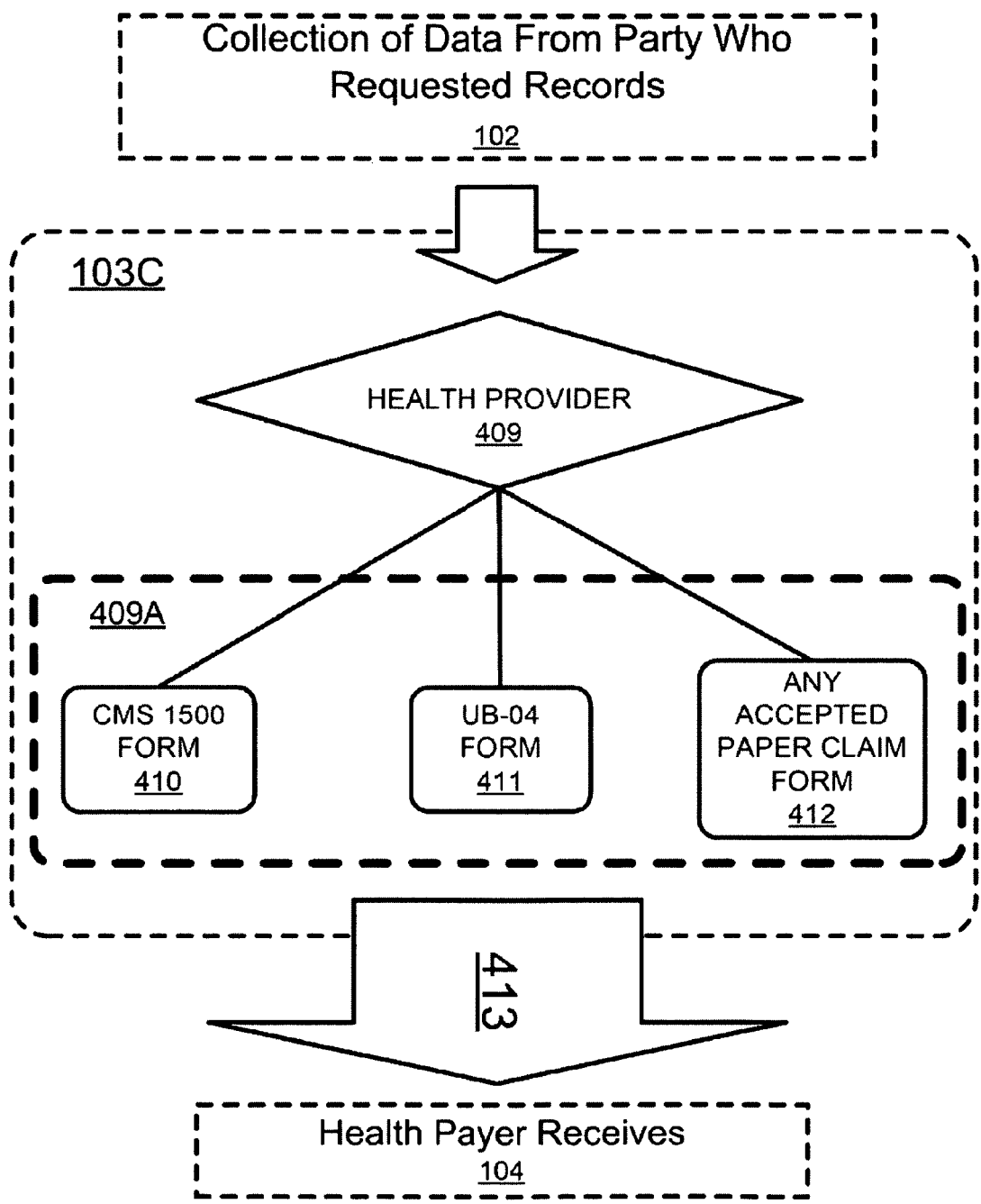
FIG. 4C is an illustration, specifying the second embodiment of the reporting process, inherent to the first embodiment of the computer-based method of data exchange.

FIG. 4C shows the second embodiment of the reporting process 103C, which takes collected data 102 gathered by the health provider 409 and transfers the data to the health insurance company 104 through a choice from a grouping of data transfer methods 409A, including of at least one of the following: a CMS 1500 form 410, a UB-04 form 411 and/or a paper claim form deemed acceptable between a health provider and health insurance company 412.

The health provider 409 makes a choice of data transfer method from grouping of data transfer methods 409A, and subsequently reports via 413, the collected data in 102 to the health insurance company, who takes possession of the data through a receiving process 104.

Figure 4D:
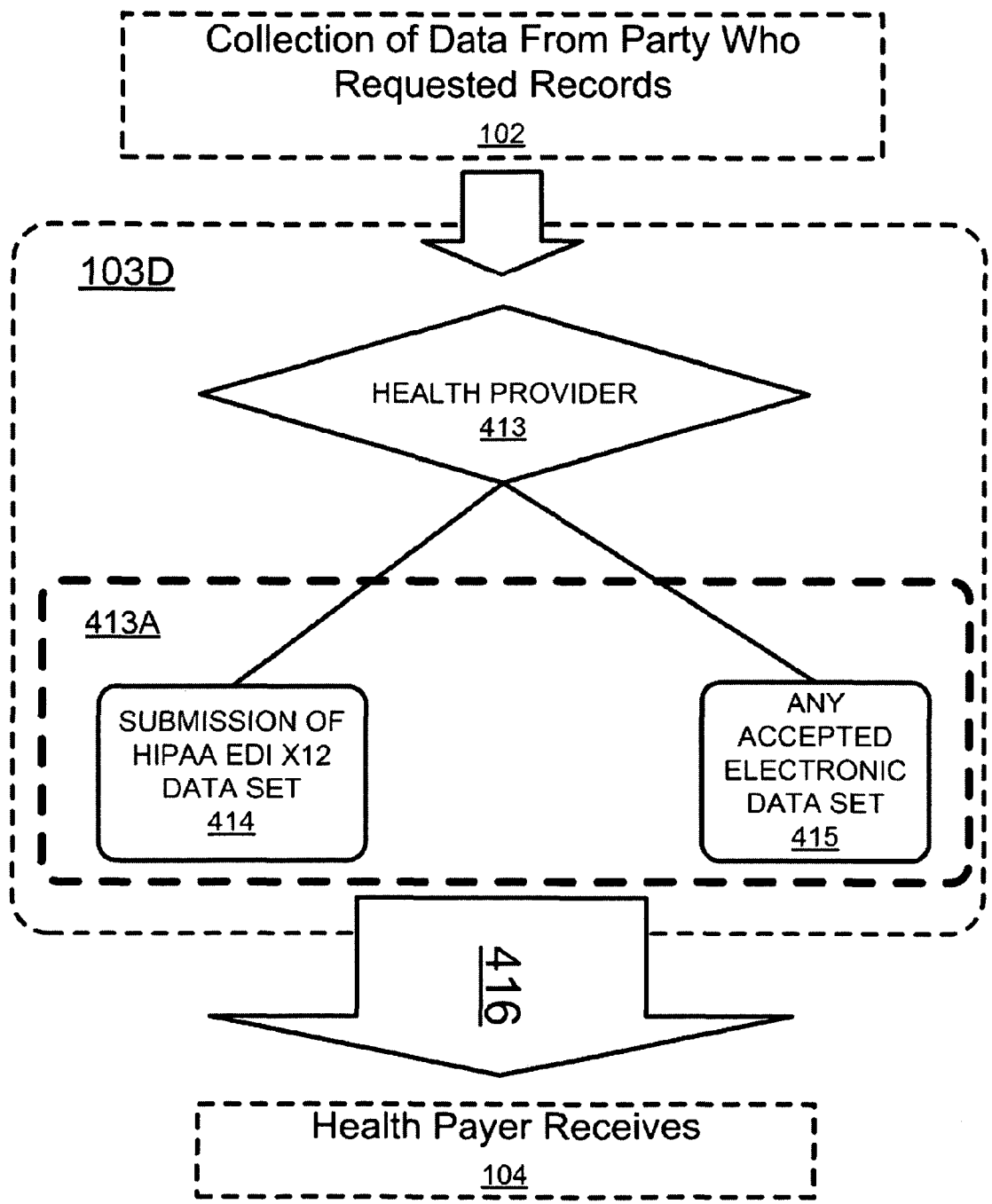
FIG. 4D is an illustration, specifying the third embodiment of the reporting process, inherent to the first embodiment of the computer-based method of data exchange.

FIG. 4D shows the third embodiment of the reporting process 103D, which takes collected data 102, gathered by the health provider 413 and transfers the data to the health insurance company 104 through a choice from a grouping of data transfer methods 413A, including of at least one of the following: submission of HIPAA EDI X12 data set 414 and/or an electronic data set claim form deemed acceptable between a health provider and health insurance company 415.

The health provider 413 makes a choice of data transfer method from grouping of data transfer methods 413A, and subsequently reports via 416, the collected data in 102 to the health insurance company, who takes possession of the data through a receiving process 104.

Figure 4E:
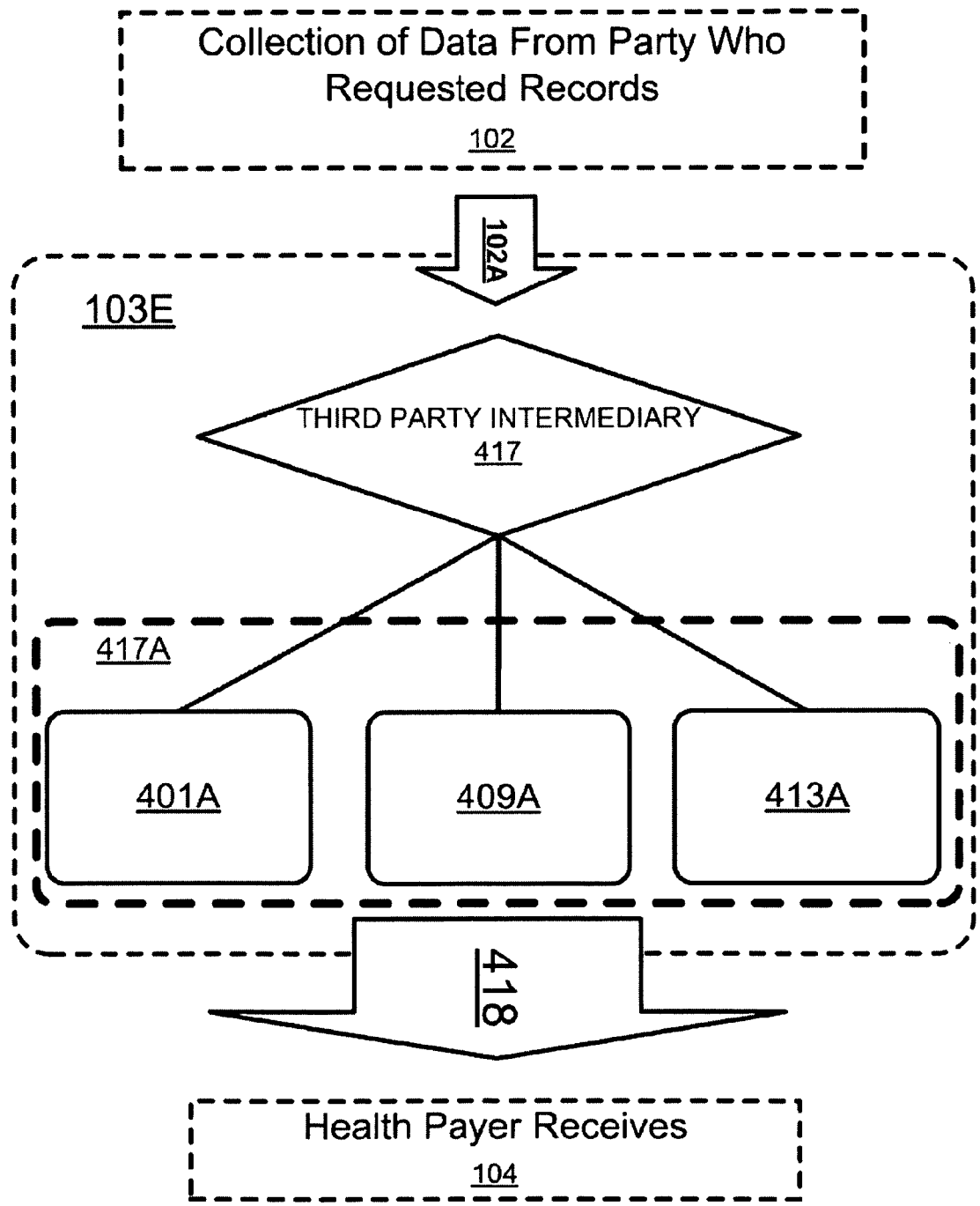
FIG. 4E is an illustration, specifying the fourth embodiment of the reporting process, inherent to the first embodiment of the computer-based method of data exchange.

FIG. 4E shows the fourth embodiment of the reporting process 103E, which takes collected data 102 and forwards the collected data via 102A to a third party intermediary 417.

The third party intermediary 417 transfers the data to the health insurance company 104 through a choice from a grouping of embodiments of the reporting process 417A, including of at least one of the following: the first embodiment of the reporting process 401A, the second embodiment of the reporting process 409A and/or the third embodiment of the reporting process 413A.

The third party intermediary 417 makes a choice of embodiment from a grouping of embodiments of the reporting process 417A, and subsequently reports via 418, the collected data in 102 to the health insurance company, who takes possession of the data through a receiving process 104.

Figure 5:
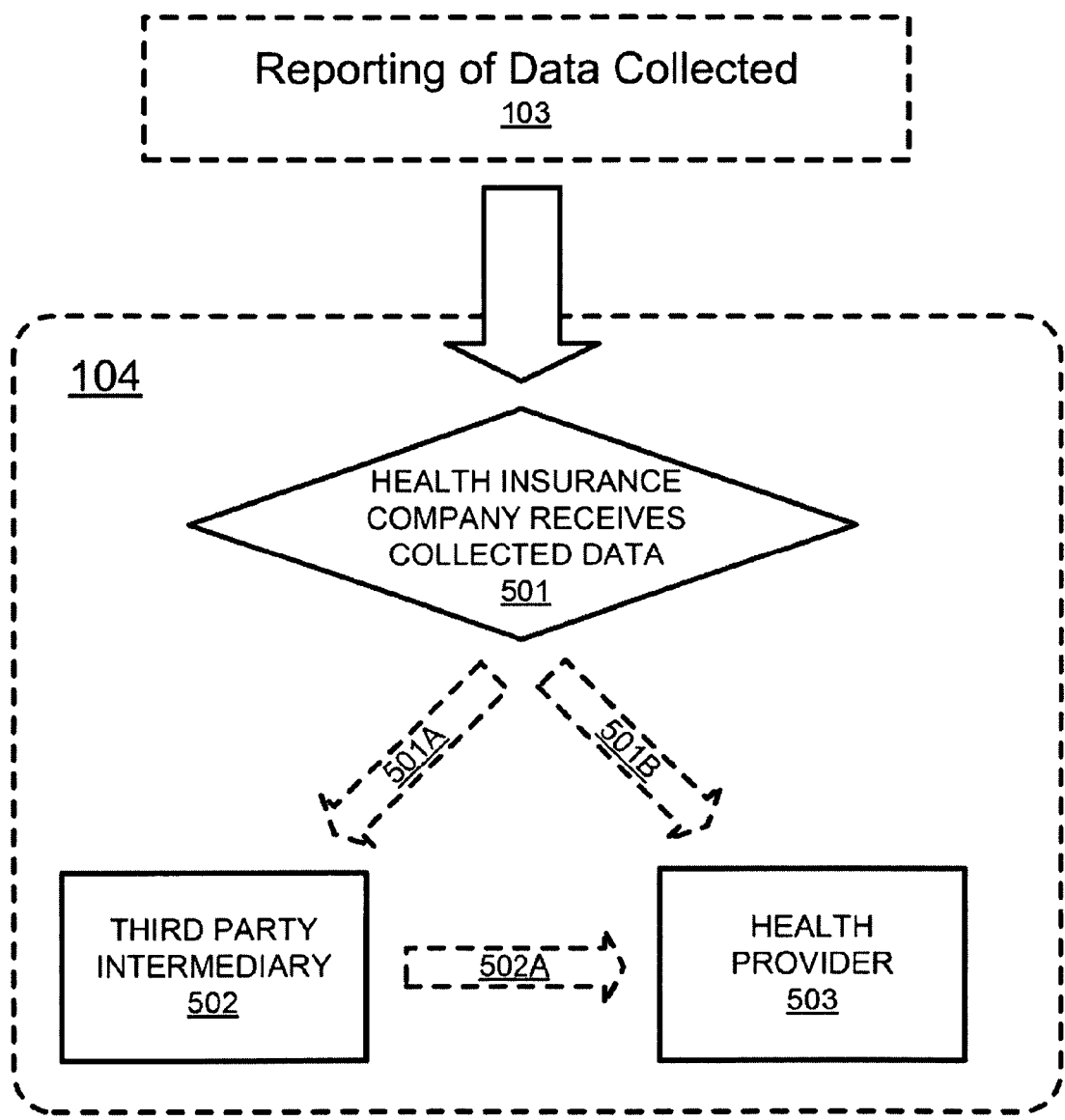
FIG. 5 is an illustration of the data receiving process, inherent to the first embodiment of the computer-based method of data exchange.

In FIG. 5, the process of receiving data 104 is specified in further detail.

In 103, the collected data is reported to the health insurance company by at least one of the following: a health provider and/or a third party intermediary.

The receiving process 104 is constituted from the health insurance company receiving data and optionally, for fair and considerable value, electing to take at least one of the following actions: the health insurance company making payment via 501A to the third party intermediary 502, who reported the collected data to the health insurance company; and optionally, the third party intermediary 502 choosing to make a portion of its collected payment 502A to health provider 503 and/or the health insurance company making payment via 501B to the health provider 503, who reported the collected data to the health insurance company.

In FIG. 6, a sample collection medium 600 is shown.

The sample collection medium is created specifically to be compliant with the processes of data collection, reporting and reception inherent to the computer-based method of the invention, specifically used at a time when a party requests patient records from a health provider.

Furthermore, the sample collection medium 600 is used in both paper and electronic formats.

Figure 7:
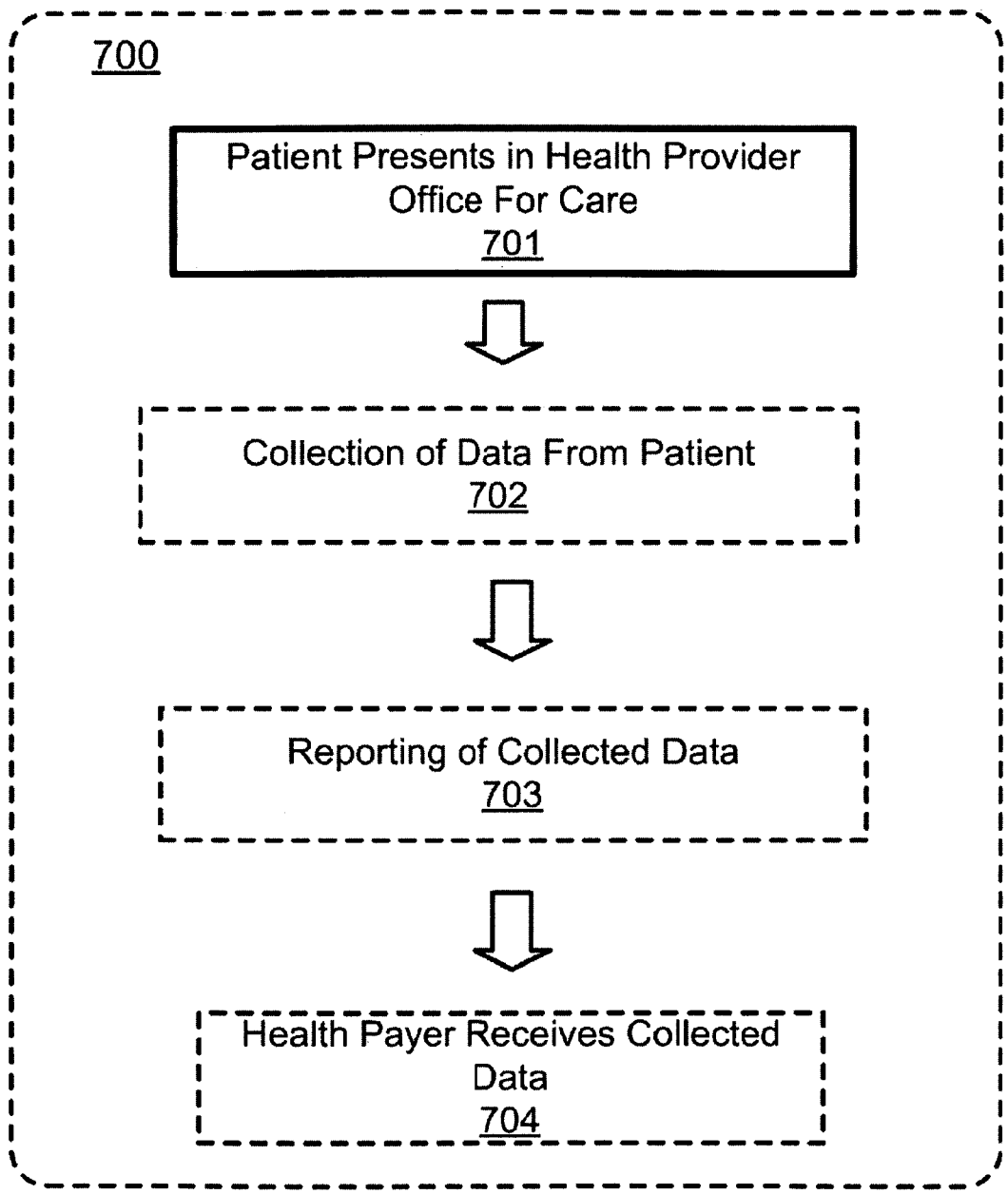
FIG. 7 is an illustration pertaining to the second embodiment of a computer-based method of data exchange between a health provider and a health insurance company, specific to data relating to a pre-treatment questionnaire completed by the patient.

According to FIG. 7, a second embodiment of the system and method 700 shows a patient presenting to a health provider's office for care 701. This occurs at a time prior to the patient receiving care or treatment from the health provider.

During this check-in or pre-treatment period, the health provider begins the process of collecting data from the patient 702. Subsequently, the health provider determines that the collected patient information is reportable to the patient's health insurance company.

The collected data is gathered, organized and subsequently goes through a reporting process to the patient's health insurance company in 703.

In the receiving process 704, the patient's health insurance company receives the data, obtained through the collection process 702 and sent to the patient's health insurance company via the reporting process 703.

Figure 8:
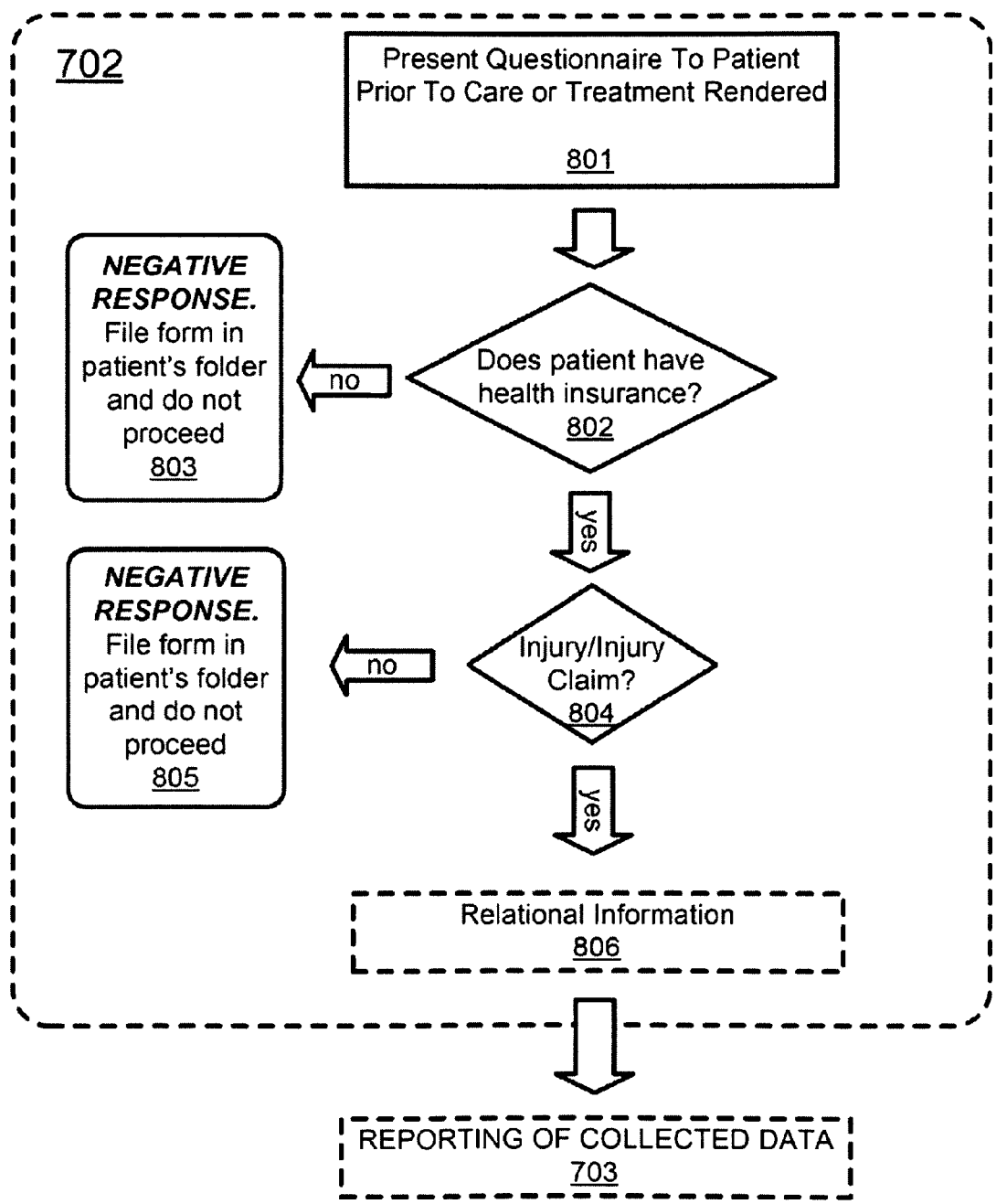
FIG. 8 is an illustration of the data collection process, inherent to the second embodiment of the computer-based method of data exchange.

In FIG. 8, the process of data collection 702 is further specified in detail.

Process 702 begins with the health provider presenting a questionnaire to the patient 801. The questionnaire is either an electronic or a paper document, designed specifically as a medium to collect patient data related to the embodiment of the method herein.

The medium used in data collection process 702 has a number of questions, which the patient completes, when applicable.

The first question of the questionnaire 802, asks if the patient has health insurance coverage. If the patient answers negatively, either the questionnaire is filed away or discarded 803, the process of data collection is both halted, and the questionnaire is deemed as data, not reportable to the patient's health insurance company.

If the patient answers positively to the first question of the questionnaire 802, then the patient proceeds to answer the second question of the questionnaire 804, which asks the patient if they are seeking care on the present visit because of at least one of the following: an injury involving another person or entity, an injury claim or lawsuit for which the patient has retained or plans to retain an attorney, an injury claim that the patient plans to file to an insurance company responsible for their injury or a large lawsuit where the patient is one of many parties suing a single business or industry (class-action lawsuit).

If the patient answers negatively, then either the questionnaire is filed away or discarded 805, the process of data collection is both halted, and the questionnaire is deemed as data, not reportable to the patient's health insurance company.

If the patient answers positively to second question of the questionnaire 804, then the patient fills out the relational information 806, as part of questionnaire in 801. Subsequent to the completion of the relational information portion of the questionnaire 806, the health provider reports the data collected to the patient's health insurance company through process 703.

Figure 9:
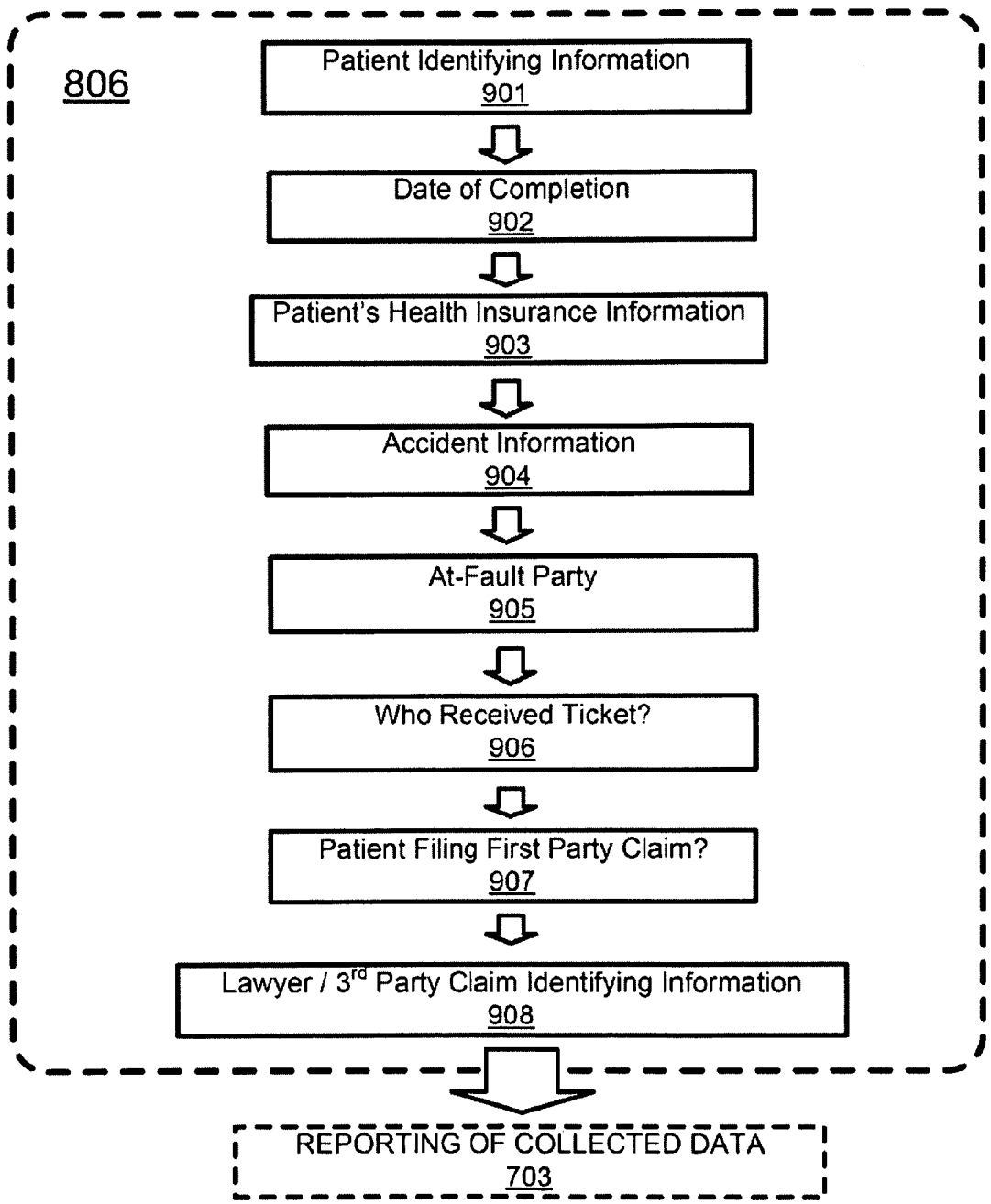
FIG. 9 is an illustration, identifying the relational information portion of the data collection process, inherent to the second embodiment of the computer-based method of data exchange.

FIG. 9 shows the relational information portion of questionnaire 806 in greater specificity, inclusive of a number of underlying queries.

The first query 901 of the relational information portion of the questionnaire 806 requests the identifying information of the patient, including the patient name, social security number and home state of residence.

The second query 902 of the relational information portion of the questionnaire 806 requests the patient note the current date on which they are filling out the questionnaire.

The third query 903 of the relational information portion of the questionnaire 806 requests the patient's health insurance information, which includes the name of the patient's health insurance company, the policy number and the group number of their health plan.

The fourth query 904 of the relational information portion of the questionnaire 806 requests accident information, including the date of the accident/injury and the state in which the accident/injury happened.

The fifth query 905 of the relational information portion of the questionnaire 806 requests the at-fault party relating to the patient's injury/accident. If the patient's injury was work-related and the patient gives the name of the company at which the patient was injured, this information is also included in 905.

The sixth query 906 of the relational information portion of the questionnaire 806 assumes that if the patient had an injury relating to a vehicular accident, that the patient attest to if either they or the other involved driver(s) received a ticket from a law officer regarding fault in the vehicular accident.

The seventh query 907 of the relational information portion of the questionnaire 806 requests the patient's attestation relating to whether or not they are filing a first party injury claim. The first party injury claim includes a patient's attestation that the filing of the claim was to at least one of the following: Med Pay, Personal Injury Protection (PIP), Uninsured Motorist, Underinsured Motorist or No-Fault.

The eighth query 908 of the relational information portion of the questionnaire 806 requests the patient's attestation to whether or not they have secured an attorney and/or if the patient has an active third party claim with a responsible non-health insurance company.

Moreover, if the patient attests positively to query 908 for having an attorney, then they complete the identifying information relating to the attorney, including the attorney's name, phone number and address.

If the patient attests positively to query 908 for having an active injury claim with a third party insurance company, then they complete identifying information relating to the injury claim number and third party insurance company name.

After the completion of all the queries as part of the relational information portion of the questionnaire 806, the health provider reports the collected data through process 703.

Figure 10A:
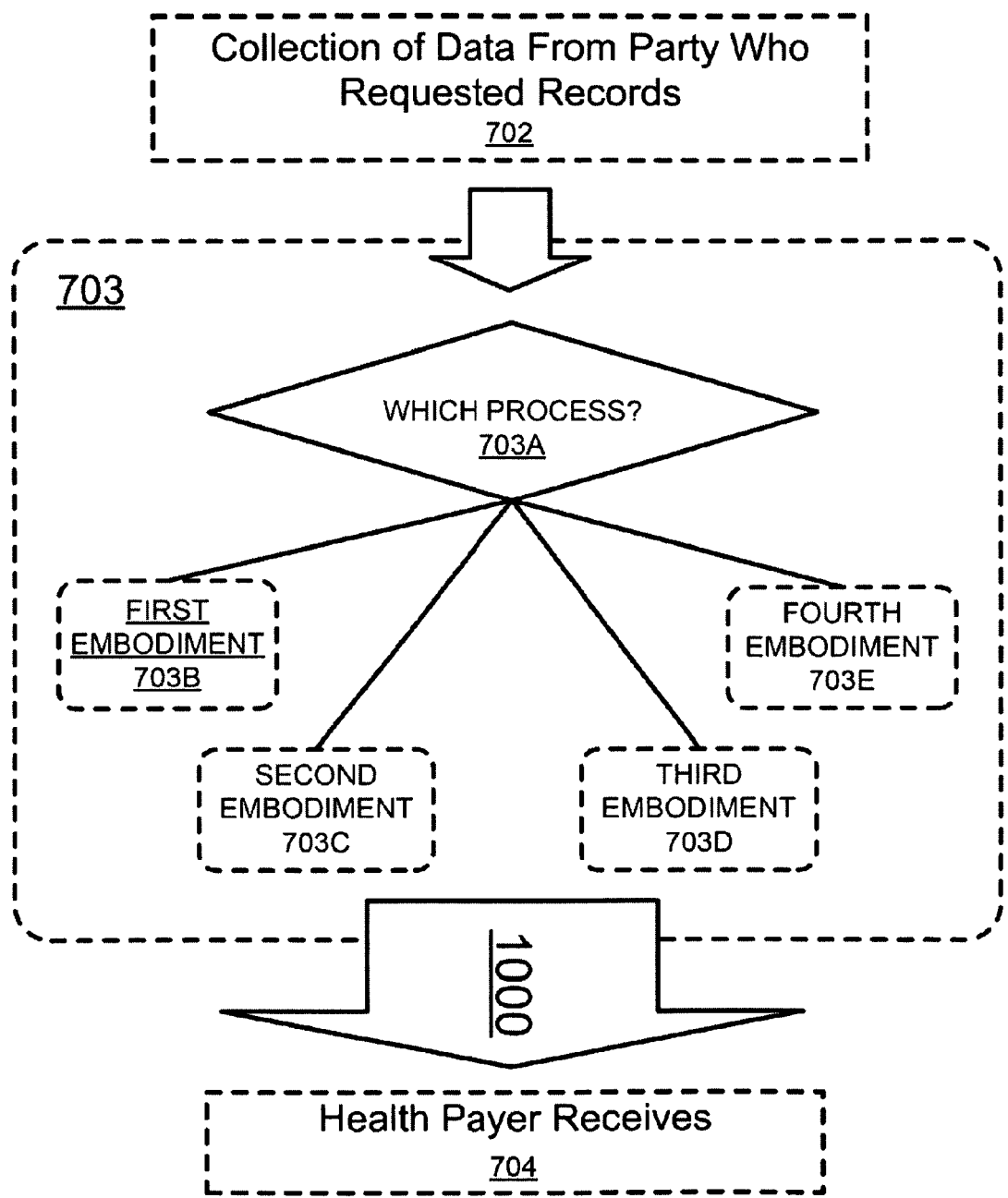
FIG. 10A is an illustration, demonstrating four different embodiments of the reporting process, inherent to the second embodiment of the computer-based method of data exchange.

FIG. 10A demonstrates the collected data 702 sent to the patient's health insurance company 704 through a reporting process 703. Moreover, in 703A, the health provider chooses one of the different embodiments of the reporting process 703, where the embodiments of the reporting process include 703B, 703C, 703D and 703E.

The health provider makes a choice of embodiment process and subsequently reports via 1000, the collected data in 702 to the health insurance company, who takes possession of the data through a receiving process 704.

Figure 10B:
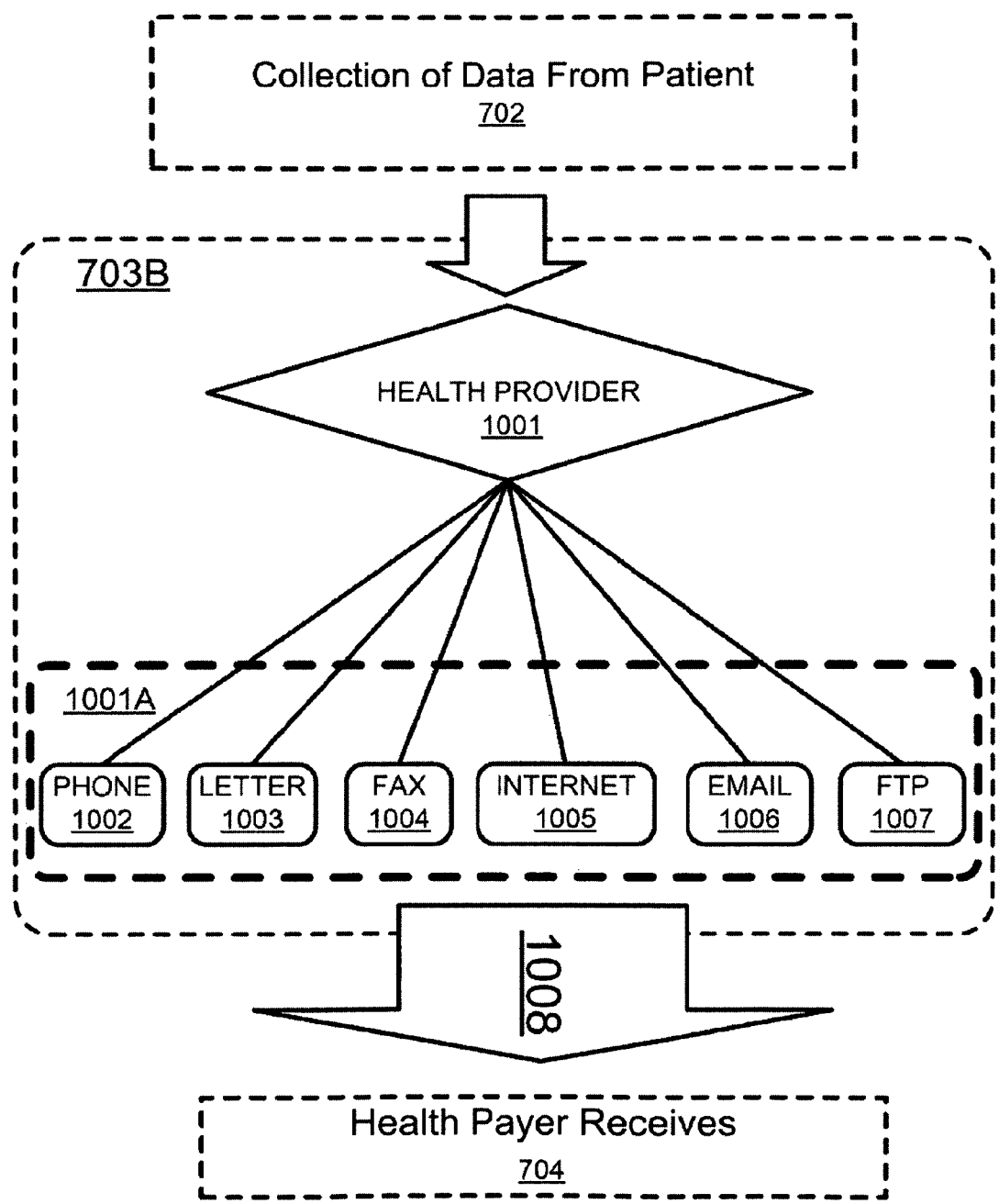
FIG. 10B is an illustration, specifying the first embodiment of the reporting process, inherent to the second embodiment of the computer-based method of data exchange.

FIG. 10B shows the first embodiment of the reporting process 703B, which takes collected data 702 gathered by the health provider 1001 and transfers the data to the health insurance company 704 through a choice from a grouping of data transfer methods 1001A, including of at least one of the following: phone 1002, letter 1003, fax 1004, internet 1005, email 1006 and/or file transfer protocol (FTP) 1007.

The health provider 1001 makes a choice of data transfer method from grouping of data transfer methods 1001A, and subsequently reports via 1008, the collected data in 702 to the health insurance company, who takes possession of the data through a receiving process 704.

Figure 10C:
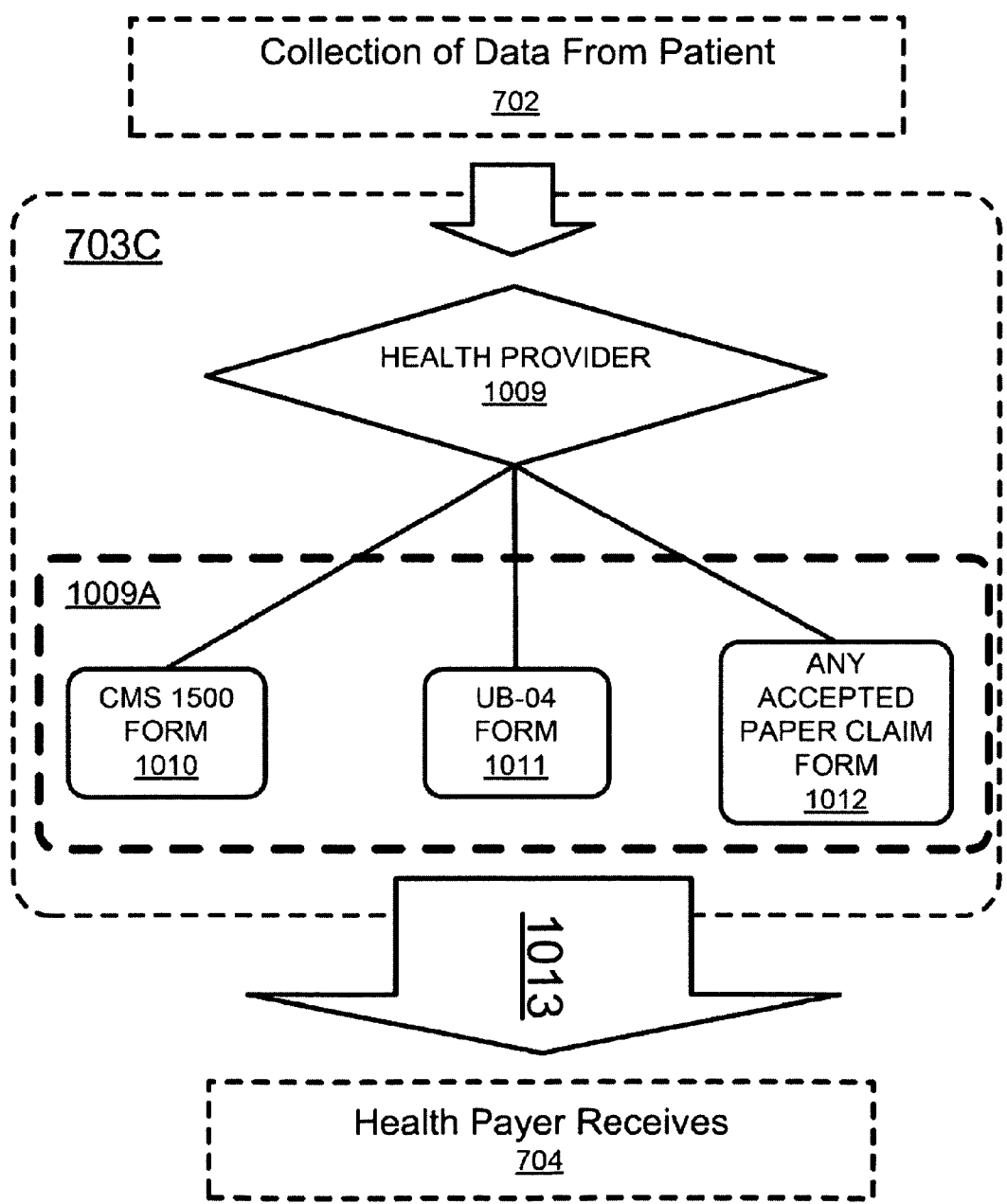
FIG. 10C is an illustration, specifying the second embodiment of the reporting process, inherent to the second embodiment of the computer-based method of data exchange.

FIG. 10C shows the second embodiment of the reporting process 703C, which takes collected data 702 gathered by the health provider 1009 and transfers the data to the health insurance company 704 through a choice from a grouping of data transfer methods 1009A, including of at least one of the following: a CMS 1500 form 1010, a UB-04 form 1011 and/or a paper claim form deemed acceptable between a health provider and health insurance company 1012.

The health provider 1009 makes a choice of data transfer method from grouping of data transfer methods 1009A, and subsequently reports via 1013, the collected data in 702 to the health insurance company, who takes possession of the data through a receiving process 704.

Figure 10D:
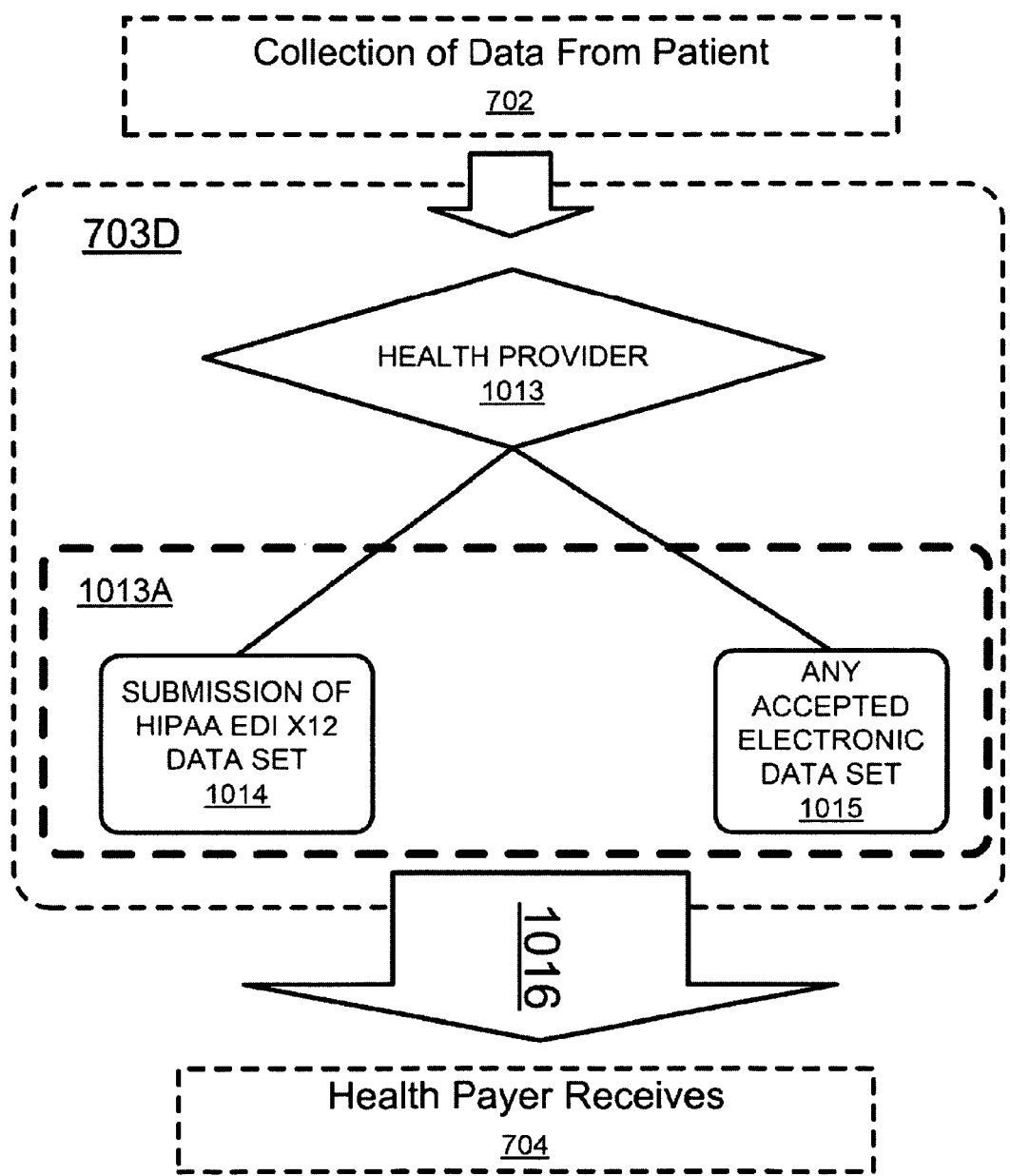
FIG. 10D is an illustration, specifying the third embodiment of the reporting process, inherent to the second embodiment of the computer-based method of data exchange.

FIG. 10D shows the third embodiment of the reporting process 703D, which takes collected data 702, gathered by the health provider 1013 and transfers the data to the health insurance company 704 through a choice from a grouping of data transfer methods 1013A, including of at least one of the following: submission of HIPAA EDI X12 data set 1014 and/or an electronic data set claim form deemed acceptable between a health provider and health insurance company 1015.

The health provider 1013 makes a choice of data transfer method from grouping of data transfer methods 1013A, and subsequently reports via 1016, the collected data in 702 to the health insurance company, who takes possession of the data through a receiving process 704.

Figure 10E:
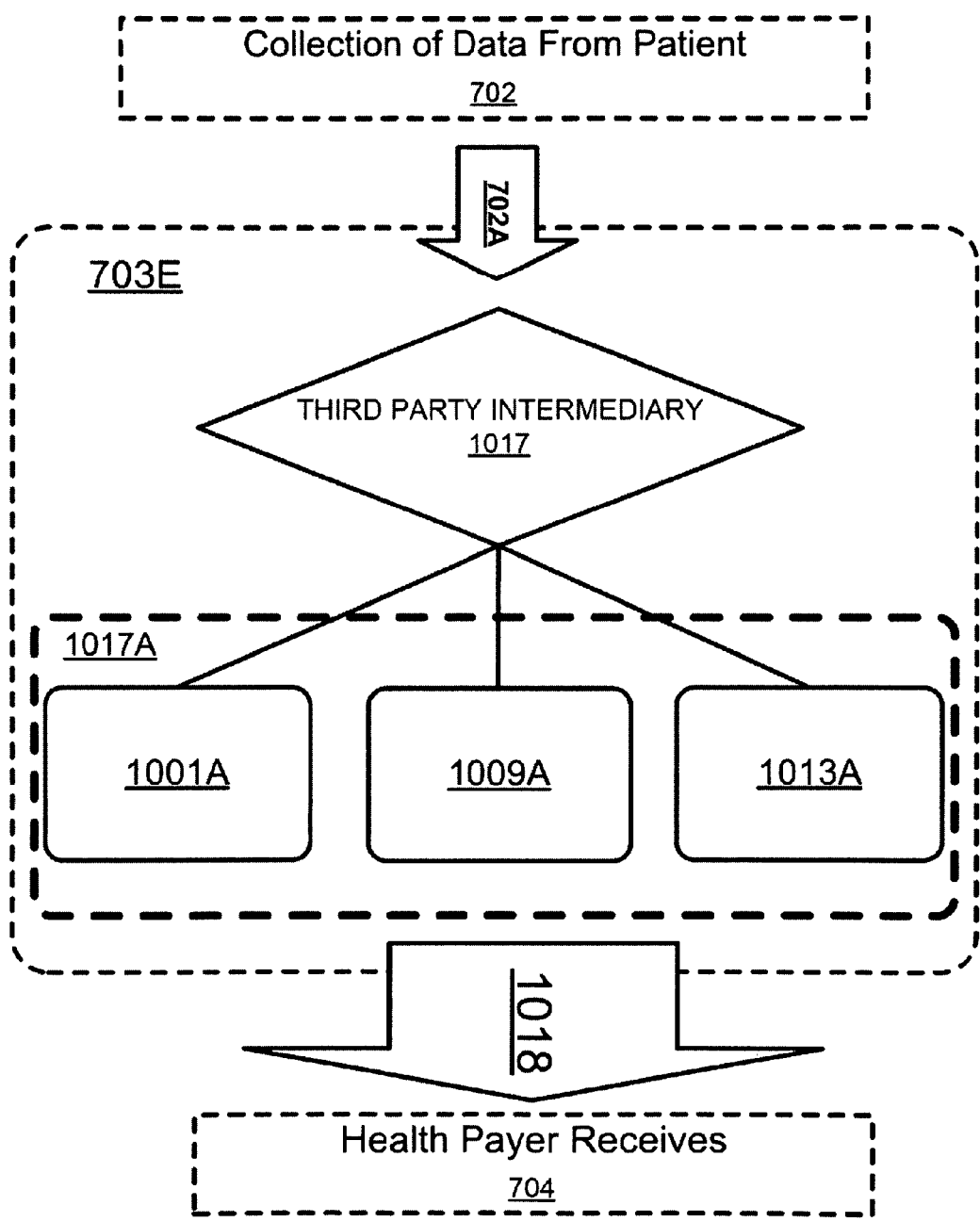
FIG. 10E is an illustration, specifying the fourth embodiment of the reporting process, inherent to the second embodiment of the computer-based method of data exchange.

FIG. 10E shows the fourth embodiment of the reporting process 703E, which takes collected data 702 and forwards the collected data via 702A to a third party intermediary 1017.

The third party intermediary 1017 transfers the data to the health insurance company 704 through a choice from a grouping of embodiments of the reporting process 1017A, including of at least one of the following: the first embodiment of the reporting process 1001A, the second embodiment of the reporting process 1009A and/or the third embodiment of the reporting process 1013A.

The third party intermediary 1017 makes a choice of embodiment from a grouping of embodiments of the reporting process 1017A, and subsequently reports via 1018, the collected data in 702 to the health insurance company, who takes possession of the data through a receiving process 704.

Figure 11:
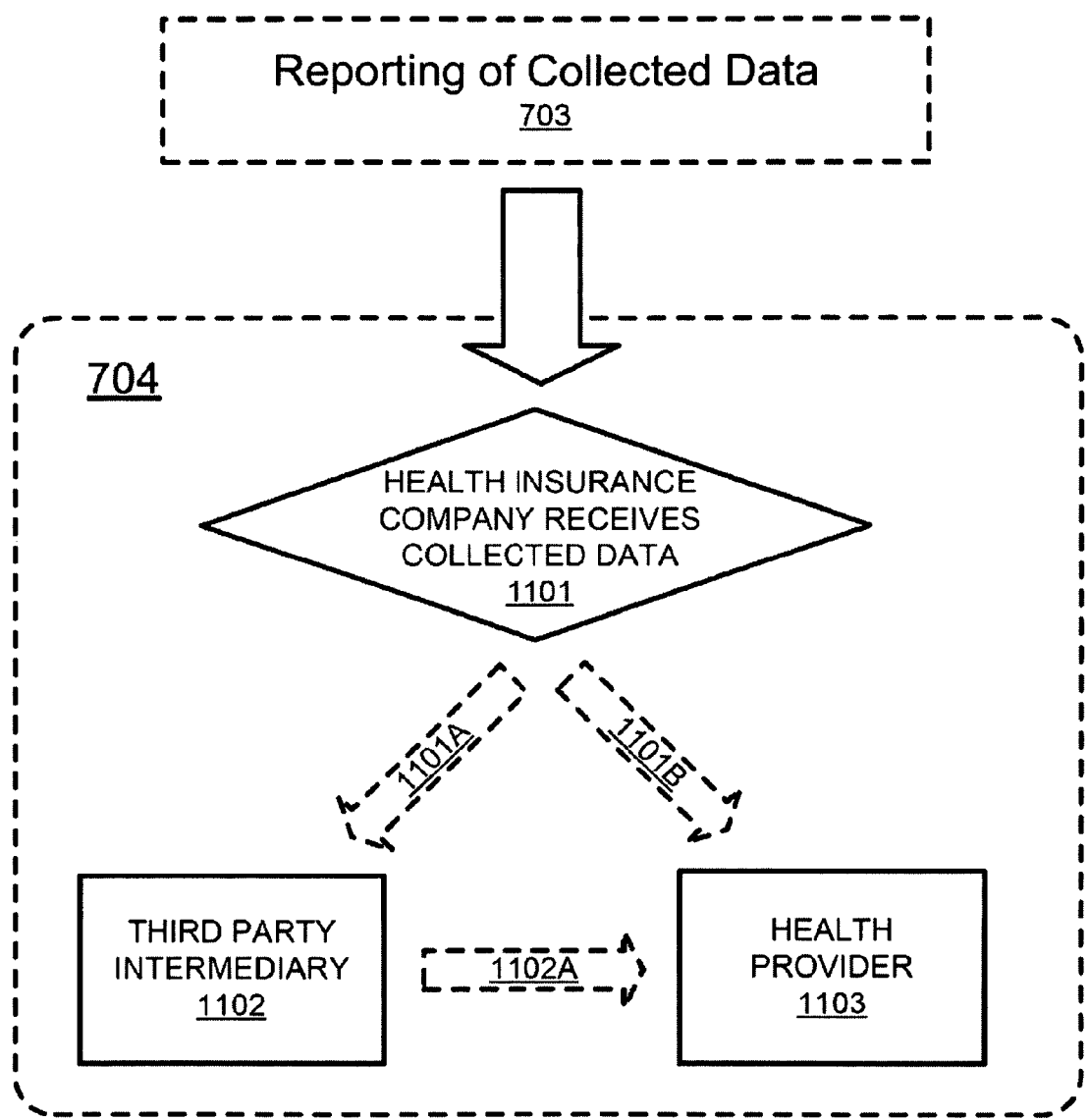
FIG. 11 is an illustration of the data receiving process, inherent to the second embodiment of the computer-based method of data exchange.

In FIG. 11, the process of receiving data 704 is specified in further detail.

In 703, the collected data is reported to the health insurance company by at least one of the following: a health provider and/or a third party intermediary.

Consequently, in 1101 the health insurance company receives the collected data.

The receiving process 704 is constituted from the health insurance company receiving data, and optionally, for fair and considerable value, electing to take at least one of the following actions: making payment via 1101A to the third party intermediary 1102, who reported the collected data to the health insurance company; and optionally, the third party intermediary 1102 chooses to make a portion of payment 1102A to health provider 1103 and/or the health insurance company making payment via 1101B to the health provider 1103, who reported the collected data to the health insurance company.

In FIG. 12, a sample questionnaire medium 1200 is shown.

The sample questionnaire medium is created specifically to be compliant with the processes of data collection, reporting and reception inherent to the computer-based method of the invention, specifically used at a time, when a patient presents prior to health provider treatment during registration or check-in period.

Furthermore, the sample questionnaire medium 1200 is used in both paper and electronic formats.

In this specification, "a" and "an" and similar phrases are to be interpreted as "at least one" and "one or more."

Many of the elements described in the disclosed embodiments may be implemented as modules. A module is defined here as an isolatable element that performs a defined function and has a defined interface to other elements. The modules described in this disclosure may be implemented in hardware, software, firmware, wetware (i.e hardware with a biological element) or a combination thereof, all of which are behaviorally equivalent. For example, modules may be implemented as a software routine written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The disclosure of this patent document incorporates material, which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In addition, it should be understood that any figures, which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A non-transitory computer readable medium storing a series of instructions, that when executed by one or more processors, causes the one or more processors to perform a method of managing request of information (ROI) data, the method comprising:
   a) receiving a record request on a patient, wherein the request is for the health provider's records on the patient, wherein the request is made by a party who is at least one of the following:
      i) the patient;
      ii) an attorney;
      iii) a defendant in a claim, where the patient is the injured claimant;
      iv) law enforcement
      v) a liability insurance company; or
      vi) a combination of the above;
   b) storing the record request made by the party;
   c) determining whether the patient received care from the health care provider applicable to an injury claim by analyzing, auditing, or tracing a previously submitted health financial record and determining whether the previously submitted health financial record is applicable to the injury claim;
   d) determining whether the patient has a responsible payment party other than the patient's health insurance company for the injury claim;
   e) creating a report, by assembling the record request on the patient, the result of any other responsible payment party other than the patient's health insurance company for the injury claim, and the result for whether the previously submitted health financial record is applicable to the injury claim;
   f) the report additionally including at least one of the following:
      i) the requesting party's demographic information;
      ii) the patient's demographic information;
      iii) the patient's health plan information;
      iv) the patient's social security number; or
      v) a combination of the above;
   h) distributing the data report to the patient's health plan.

2. The non-transitory computer readable medium of claim 1, wherein the health plan is a insurance coverage plan including one of the following:
   a) Medicare;
   b) Medicare advantage;
   c) Medicare intermediaries;
   d) Medicaid;
   e) self-insured plans;
   f) group health plans;
   g) individual health plans;
   h) county health plans;
   i) state health plans;
   j) federal health plans;
   k) private union plans;
   l) workers compensation plans;
   m) medical riders on liability plans;
   n) vendors of health plans; or
   o) a combination of the above.

3. The non-transitory computer readable medium of claim 1, wherein the health provider distributes the data report to the health plan through at least one of the following:
   a) phone;
   b) letter;
   c) fax;
   d) internet;
   e) e-mail;
   f) FTP transfer;
   g) a ubiquitous and recognized paper health form, including CMS 1500 and UB-04;
   h) data code sets of HIPAA (Health Insurance Portability and Accountability Act); or
   i) a combination of the above.

4. The non-transitory computer readable medium of claim 1, wherein a data exchange intermediary creates the data report.

5. The non-transitory computer readable medium of claim 1, wherein a health provider includes at least one of the following:
   a) health systems;
   b) hospitals;
   c) outpatient facilities;
   d) physicians;
   e) non-physician health providers;
   f) suppliers of pharmaceuticals;
   g) suppliers of medical equipment;
   h) diagnostic testing companies;
   i) imaging companies;
   j) retail sellers of pharmaceutical products;
   k) any licensed individual that provides billable health care services; or
   l) a combination of the above.

6. The non-transitory computer readable medium according to claim 1, where the patient's injury claim resulted from an injury, the injury related to one of the following:
   a) a vehicular accident;
   b) a work-related accident;
   c) a slip and fall;
   d) an assault;
   e) battery;
   f) an infliction of emotional distress;
   g) nursing home abuse;
   h) sexual abuse;
   i) wrongful death;
   j) a pharmaceutical product;
   k) a defective product;
   l) medical malpractice;
   m) negligence;
   n) tobacco;
   o) poisoning;
   p) occupational disease;
   q) Mesothelioma;
   r) Radiation;
   s) dog bite;
   t) premises liability;
   u) boat/maritime accident;
   v) aviation accidents;
   w) railroad accidents;
   x) construction accidents;
   y) birth injury; or
   z) a combination of the above.

7. The non-transitory computer readable medium of claim 1, wherein the health plan uses the received data report for at least one of the following:
   a) investigation of a subrogation claim;
   b) identification of a subrogation claim;
   c) filing of a subrogation claim;

d) identification of health care providers, apart from the submitting health care provider, who also rendered care to the patient;
e) coordination of benefits (COB)
f) claims management
g) underwriting; or
h) a combination of the above.

* * * * *